United States Patent [19]

Butler et al.

[11] Patent Number: 5,332,755
[45] Date of Patent: Jul. 26, 1994

[54] NEW INDOLE DERIVATIVES, A PROCESS FOR THEIR PREPARATION AND THEIR USE IN MEDICAMENTS

[75] Inventors: John E. Butler, Wuppertal, Fed. Rep. of Germany; Nigel J. Cuthbert, Prestwood Great Missenden, United Kingdom

[73] Assignee: Bayer Aktiengesellschaft, Leverkusen, Fed. Rep. of Germany

[21] Appl. No.: 820,109

[22] Filed: Jan. 13, 1992

Related U.S. Application Data

[62] Division of Ser. No. 547,560, Jul. 2, 1990, Pat. No. 5,118,700.

[30] Foreign Application Priority Data

Jul. 21, 1989 [GB] United Kingdom ............... 8916774

[51] Int. Cl.$^5$ ............................................. A61K 31/41
[52] U.S. Cl. ..................................... 514/415; 548/494
[58] Field of Search ......................... 548/494; 514/415

*Primary Examiner*—David B. Springer
*Attorney, Agent, or Firm*—Sprung Horn Kramer & Woods

[57] ABSTRACT

Indole derivative for leucotriene antagonism of the formula

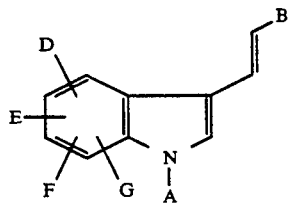

wherein groups A, B, D, E, F and G are as described in the specification.

2 Claims, No Drawings

NEW INDOLE DERIVATIVES, A PROCESS FOR THEIR PREPARATION AND THEIR USE IN MEDICAMENTS

This is a division of application Ser. No. 547,560, filed Jul. 2, 1990, now U.S. Pat. No. 5,118,700.

BACKGROUND OF THE INVENTION

1. Field of the Invention

The invention relates to new indole derivatives, a process for their preparation and their use in medicaments, in particular as leukotriene antagonists.

2. Description of Related Art

It is known that polymorphonuclear granulocytes and mast cells secrete SRS-A (Slow Reacting Substance of Anaphylaxis) mediators if, for example, they are stimulated by allergens. SRS-A is composed of the peptidoleukotrienes $LTC_4$, $LTD_4$ and $LTE_4$ which are formed from arachidonic acid in the 5-lipoxygenases pathway. The influence of the leukotrienes in allergic and inflammatory disorders can be traced back to specific receptors on the target cells (for example, smooth muscle cells). In addition, it is known that, by alterations to the structure of the leukotrienes (for example, partial saturation of the double bonds or variations in or elimination of the peptide side chain), a partial agonistic or antagonistic action can occur [compare John H. Musser et al., Agents and Actions 18, 332–341 (1986); John G. Gleason et al., J. Med. Chem. 30, (6), 959–961 (1987)].

In addition, it is known that tetrahydrocarbazole acetic acid derivatives and 1-carboxyalkylindoles and -indazoles have leukotriene-antagonistic action [compare U.S. Pat. No. 4,783,479 and EP-A 179,019].

SUMMARY OF THE INVENTION

New indole derivatives of the general formula (I)

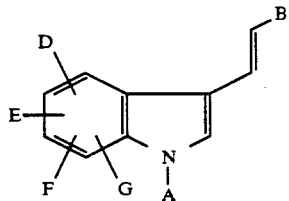

(I)

in which

A—represents a straight-chain or branched alkyl having up to 12 carbon atoms, which is optionally substituted by cycloalkyl having 3 to 8 carbon atoms, halogen, hydroxyl, carboxyl, cyano, straight-chain or branched alkoxy or alkoxycarbonyl, each having up to 10 carbon atoms or by a group of the formula $-CO-NH-SO_2-R^1$, in which $R^1$—denotes aryl having 6 to 10 carbon atoms, which is optionally monosubstituted to trisubstituted by identical or different substituents from the series comprising carboxyl, halogen, cyano, nitro or by straight-chain or branched alkyl, alkoxy or alkoxycarbonyl each having up to 10 carbon atoms, or by aryl having 6 to 10 carbon atoms, or by a 5- to 7-membered saturated or unsaturated heterocycle having up to 4 heteroatoms from the series comprising nitrogen, sulphur or oxygen, which are in turn monosubstituted to tetrasubstituted by identical or different substituents from the series comprising carboxyl, straight-chain or branched alkyl, alkylthio, alkoxy or alkoxycarbonyl, each having up to 10 carbon atoms, or by a group of the formula $-NH-R^2$, in which $R^2$—denotes hydrogen, straight-chain or branched alkyl or acyl each having up to 8 carbon atoms, B—represents straight-chain or branched alkyl, alkenyl or alkinyl having 12 to 18 carbon atoms, which is optionally substituted by halogen, mercapto, straight-chain or branched alkoxy, acyl or alkoxycarbonyl each having up to 10 carbon atoms or by aryl having 6 to 10 carbon atoms, which may in turn be monosubstituted to tetrasubstituted by identical or different substituents from the series comprising halogen, nitro, cyano, carboxyl, hydroxyl or by a group of the formula $-Y-(CH_2)_n-X-R^3$, in which X and Y are identical or different, oxygen or sulphur, or denote a direct bond, n—denotes a number 1, 2, 3, 4, 5 or 6 and $R^3$- denotes aryl having 6 to 10 carbon atoms, which is optionally substituted by hydroxyl, carboxyl, nitro, cyano, halogen or by straightchain or branched alkyl, acyl, alkoxy or alkoxycarbonyl each having up to 10 carbon atoms, or B—represents aryl having 6 to 10 carbon atoms, which is optionally monosubstituted to trisubstituted by identical or different substituents from the series comprising halogen, nitro, hydroxyl or by a group of the formula $-Y-(CH_2)_n-X-R^3$, in which X, Y, $R^3$ and n have the abovementioned meanings, D, E, F and G are identical or different and —represent hydrogen, halogen, cyano, hydroxyl or carboxyl, —represent straight-chain or branched alkyl, alkoxy, alkoxycarbonyl or acyl each having up to 10 carbon atoms or represent cycloalkyl having 3 to 8 carbon atoms, —represent a 5- to 7-membered saturated or unsaturated heterocycle having up to 4 heteroatoms from the series comprising nitrogen, sulphur or oxygen, or —represent a group of the formula $-CO-NH-SO_2-R^1$, in which $R^1$ has the abovementioned meaning, and their physiologically acceptable salts.

DETAILED DESCRIPTION OF THE INVENTION

In the context of the present invention, physiologically acceptable salts are preferred. Physiologically acceptable salts of the substituted indole derivatives may be salts of the substances according to the invention with carboxylic acids or sulphonic acids. Particularly preferred salts are, for example, those with hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, propionic acid, lactic acid, tartaric acid, citric acid, fumaric acid, maleic acid or benzoic acid. Salts in the context of the present invention are salts of the monovalent metals such as alkali metals and the ammonium salts. Sodium salts, potassium salts and ammonium salts are preferred.

The compounds according to the invention can exist in stereoisomeric forms which behave either as image and mirror image (enantiomers) or which do not behave as image and mirror image (diastereomers). The invention relates both to the antipodes and the racemates and also the mixtures of diastereomers. The racemates, like the diastereomers, can be separated in a known manner, for example, by crystallization, chromatography or Craig partition into the stereoisomerically uniform constituents (compare E.L. Eliel, Stereochemistry of Carbon Compounds, McGraw Hill, 1962).

Preferred compounds are those of the general formula (I) in which

A—represents straight-chain or branched alkyl having up to 10 carbon atoms, which is optionally substituted by cyclopropyl, cyclopentyl, cyclohexyl, fluorine, chlorine, bromine, hydroxyl, carboxyl, cyano, straight-chain or branched alkoxy or alkoxycarbonyl each having up to 8 carbon atoms or by a group of the formula —CO—NH—SO$_2$—R$^1$,
in which R$^1$—denotes phenyl or naphthyl, each of which is optionally monosubstituted or disubstituted by identical or different substituents from the series comprising carboxyl, fluorine, chlorine, bromine, cyano, nitro or by straight-chain or branched alkyl, alkoxy or alkoxycarbonyl each having up to 8 carbon atoms, or by phenyl, naphthyl, thienyl, furyl, pyridyl, pyrimidyl, quinolyl, isoquinolyl,. pyrryl, imidazolyl, 1,3-thiazolyl, tetrazolyl, oxazolyl, isoxazolyl, isothiazolyl, triazolyl or thiadiazolyl, which are in turn monosubstituted to trisubstituted by identical or different substituents from the series comprising carboxyl, straight-chain or branched alkyl, alkylthio, alkoxy or alkoxycarbonyl each having up to 8 carbon atoms or by a group of the formula —NH—R$^2$,
in which R$^2$—denotes hydrogen, or straight-chain or branched alkyl or acyl each having up to 6 carbon atoms, B—represents straight-chain or branched alkyl or alkenyl each having 12 to 16 carbon atoms, each of which optionally substituted by fluorine, chlorine, bromine, carboxyl, hydroxyl, straight-chain or branched alkoxy, acyl or alkoxycarbonyl each having up to 8 carbon atoms, or by phenyl, which may in turn be monosubstituted to trisubstituted by identical or different substituents from the series comprising fluorine, chlorine, bromine, carboxyl, cyano, hydroxyl or by a group of the formula —Y—(CH$_2$—X—R$^3$,
in which X and Y are identical or different, oxygen or sulphur, or denote a direct bond, n—denotes a number 1, 2, 3, 4, 5 or 6
and R$^3$—denotes phenyl or naphthyl, each of which is optionally substituted by hydroxyl, carboxyl, cyano, fluorine, chlorine, bromine or by straight-chain or branched alkoxy, acyl or alkoxycarbonyl each having up to 8 carbon atoms,
or B—represents phenyl which is optionally monosubstituted or disubstituted by identical or different substituents from the series comprising fluorine, chlorine, bromine, nitro, hydroxyl or by a group of the formula —Y—(CH$_2$)$_n$—X—R$^3$,
in which X, Y, n and R$^3$ have the abovementioned meanings, D, E, F and G are identical or different and —represent, hydrogen, fluorine, chlorine, bromine, cyano, carboxyl, straight-chain or branched alkyl, acyl or alkoxycarbonyl each having up to 8 carbon atoms, thienyl, furyl, pyridyl, pyrimidyl, quinolyl, isoquinolyl, pyrryl, imidazolyl, 1,3-thiazolyl, tetrazolyl, oxazolyl, isoxazolyl, isothiazolyl, triazolyl, thiadiazolyl or —represent a group of the formula —CO—NH—SO$_2$—R$^1$, in which R$^1$ has the abovementioned meaning, and their physiologically acceptable salts.

Particularly preferred compounds are those of the general formula (I) in which

A—represents straight-chain or branched alkyl having up to 8 carbon atoms, which is- optionally substituted by carboxyl, cyano, straight-chain or branched alkoxycarbonyl having up to 6 carbon atoms or by a group of the formula —CO—NH—SO$_2$—R$^1$, in which R$^1$—denotes phenyl which is optionally substituted by cyano, carboxyl or by straight-chain or branched alkyl or alkoxycarbonyl each having up to 6 carbon atoms, or by phenyl, thienyl, furyl, pyrryl, 1,3-thidazolyl, tetrazolyl, oxazolyl, isoxazolyl, isothiazolyl, triazolyl or thiadiazolyl, B—represents straight-chain or branched alkyl or alkenyl, having 12 carbon atoms, each of which is optionally substituted by carboxyl, acetyl, propanoyl, straight-chain or branched alkoxy or alkoxycarbonyl each having up to 6 carbon atoms or by phenyl, which may in turn be monosubstituted or disubstituted by identical or different substituents from the series comprising cyano, carboxyl or by a group of the formula —Y—(CH$_2$)$_n$—X—R$^3$,
in which X and Y are identical or different, oxygen or sulphur, or denote a direct bond, n—denotes a number 2, 3 or 4
and R$^3$—denotes phenyl which is optionally substituted by hydroxyl, cyano, acetyl, propanoyl, carboxyl or by alkoxycarbonyl having up to 6 carbon atoms, or B—represents phenyl which is substituted by a group of the formula —Y—(CH$_2$)$_n$—X—R$^3$,
in which X, Y, n and R$^3$ have the abovementioned meanings, D, E and F represent hydrogen and G—represents cyano, carboxyl, alkoxycarbonyl having up to 6 carbon atoms, thienyl, furyl, tetrazolyl, triazolyl or —represents a group of the formula —CO—NH—SO$_2$—R$^1$, in which R$^3$ has the abovementioned meaning, and their physiologically acceptable salts.

The compounds of the general formula (I) according to the invention are prepared by reacting aldehydes of the general formula (II)

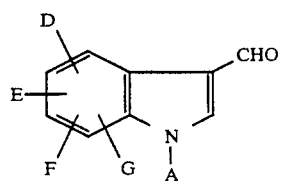

(II)

in which

D, E, F, G and A have the abovementioned meanings, with phosphorus compounds of the general formula (III), $$\oplus P(R^4)_3CH_2B[Z]\ominus \quad \text{(III)}$$

(IV) and (V)

$$\underset{\underset{O}{\overset{R^4}{|}}}{B-CH_2-\overset{R^4}{\underset{\|}{P}}-R^5} \quad \text{(IV)}$$

or $$B-CH_2-\underset{\underset{O}{\|}}{\overset{OR^4}{\overset{|}{P}}}-OR^5 \quad \text{(V)}$$

in which
B—has the abovementioned meaning,
$R^4$ and $R^5$ are identical or different and denote ($C_1$—$C_6$)—alkyl or phenyl
and
Z—represents chlorine, bromine, iodine or the tosylate anion,
in inert solvents, if appropriate in the presence of bases and, in the case of the acids, hydrolyzing the esters by customary methods.

The process is illustrated by way of example in the following equation:

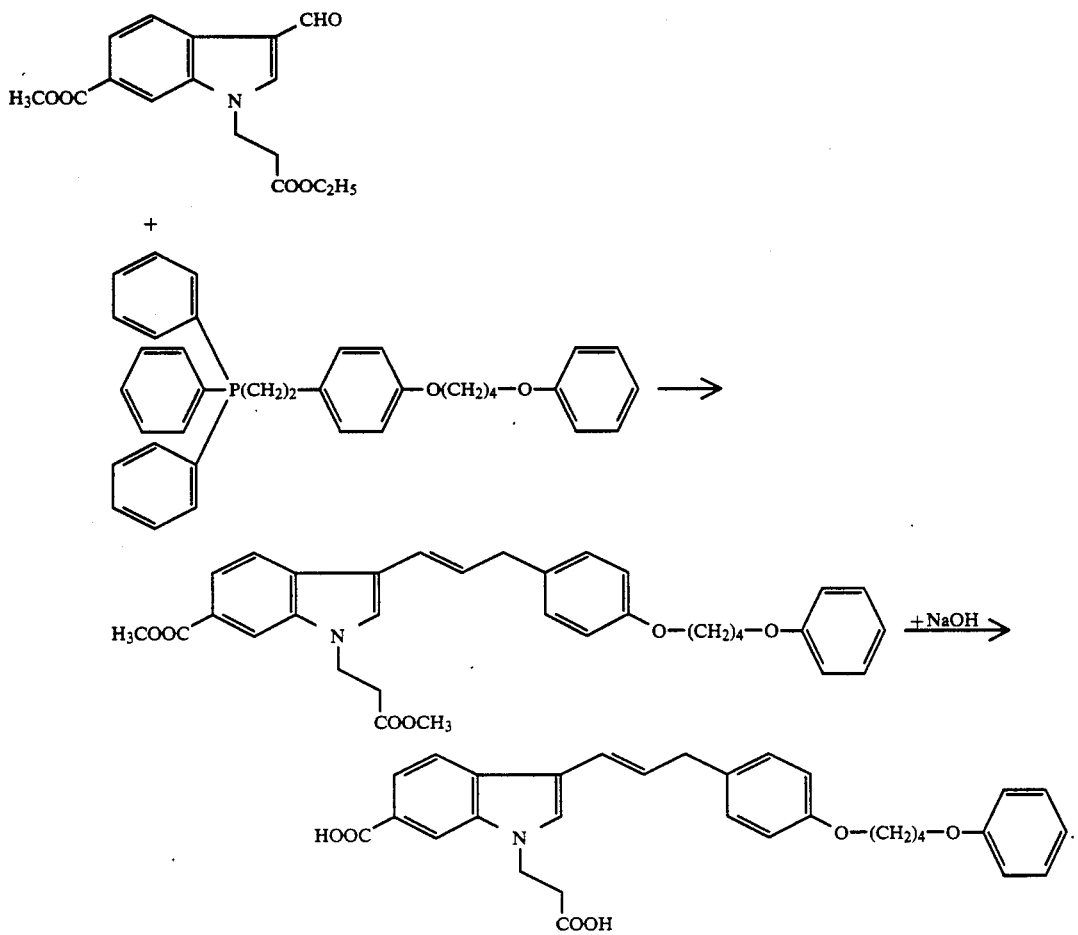

Suitable solvents are the customary organic solvents which do not change under the reaction conditions. Ethers such as, for example, diethyl ether, butyl methyl ether, dioxane, tetrahydrofuran, glycol dimethyl ether or ethylene glycol dimethyl ether, or hydrocarbons such as, for example, benzene, toluene or xylene, or amides such as, for example, dimethylformamide or hexamethylphosphoramide, or 1,3-dimethylimidazolidin-2-one, 1,3-dimethyl-tetrahydro-pyridin-2-one or dimethyl sulphoxide are preferred. It is also possible to use mixtures of the abovementioned solvents. Tetrahydrofuran and dimethylformamide are preferred.

Suitable bases for the Wittig reaction are customary organic and inorganic bases. These preferably include alkali metal hydrides such as, for example, sodium hydride or potassium hydride, or alkali metal alkoxides such as, for example, sodium methoxide, sodium ethoxide, potassium methoxide, potassium ethoxide or potassium tert.butoxide, or amides such as, for example, sodium amide or lithium diisopropylamide, or organic lithium compounds such as phenyllithium, butyllithium or methyllithium or sodium hexamethylsilazane. Potassium tert.-butoxide, phenyllithium or butyllithium are preferred.

The phosphorus compounds (III), (IV) and (V) are generally employed in an amount from i to 2 moles, preferably in molar amounts, relative to 1 mole of the aldehyde (II). The base is generally employed in an amount from 1 to 5 moles, preferably from i to 2 moles, relative to 1 mole of the phosphorus compounds.

The Wittig reaction generally proceeds in a temperature range from −80° C. to +40° C., preferably from −80° C. to +10° C. at atmospheric, elevated or reduced pressure, preferably at atmospheric pressure.

The Wittig reaction can either be carried out in a two-step reaction or in a one-step process: in the two-step reaction, the phosphoranes $[(R^4)_3P=CH_2—B]$ are first prepared from the corresponding phosphonium salts under the action of bases and these are then reacted with the aldehydes (II). In the one step reaction, which is preferred, the salts of the compounds of the formula (III) react directly with the aldehydes (II) in the presence of a base.

Suitable bases for the hydrolysis are the customary inorganic bases. These preferably include alkali metal hydroxides or alkaline earth metal hydroxides such as, for example, sodium hydroxide, potassium hydroxide, lithium hydroxide or barium hydroxide, or alkali metal carbonates such as sodium carbonate or potassium carbonate. Particularly preferably, sodium hydroxide or lithium hydroxide are employed.

Suitable solvents for the hydrolysis are water or the organic solvents customary for hydrolysis. These preferably include alcohols such as methanol, ethanol, propanol, isopropanol or butanol, or ethers, such as tetrahydrofuran or dioxane, or dimethylformamide or dimethyl sulphoxide. Particularly preferably, alcohols such as methanol, ethanol, propanol or isopropanol are used. It is also possible to employ mixtures of the solvents mentioned.

The hydrolysis Is generally carried out in a temperature range from 0° C. to +100° C., preferably at room temperature. In general, the hydrolysis is carried out at atmospheric pressure. However, it is also possible to work at reduced pressure or at elevated pressure (for example from 0.5 to bar).

When carrying out the hydrolysis, the base is generally employed in an amount from 1 to 3 moles, preferably from 1 to 1.5 moles, relative to I mole of the ester or the lactone. Particularly preferably, molar amounts of reactants are used.

When carrying out the reaction, the salts of the compounds according to the invention are formed in the first step as intermediates which can be isolated. The acids according to the invention are obtained by treating the salts with customary inorganic acids. These preferably include mineral acids such as, for example, hydrochloric acid, hydrobromic acid, sulphuric acid or phosphoric acid. It has proved advantageous in the preparation of the carboxylic acids to acidify the basic reaction mixture from the hydrolysis in a second step without isolation of the salts. The acids can then be isolated in a customary manner.

The aldehydes of the general formula (II) are new and can be prepared by reacting compounds of the general formula (VI)

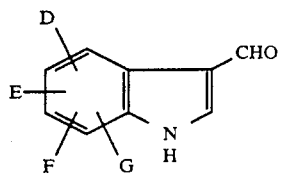

(VI)

in which

D, E, F and G have the abovementioned meanings, with compounds of the general formula (VII)

Hal-A   (VII)

in which

Hal represents fluorine, chlorine, bromine or iodine and

A has the abovementioned meaning, in inert solvents, if appropriate in the presence of a base and, in the case of the acids, hydrolyzing the esters by the methods indicated above.

When carrying out the reaction, the solvents and bases mentioned above in connection with the Wittig reaction can be employ&d.

The compounds of the general formula (VI) are known per se or can be prepared by known methods, for example by formulation of the corresponding indole with phosphorus oxychloride in dimethylformamide [compare H. Büttcher, R. Gericke, Liebigs Ann. Chem. 1988, 749–752; Organikum (Organic Compounds) p. 405, VEB Deutscher Verlag der Wissenschaften, Berlin 1977].

The compounds of the general formulae (III), (IV) and (V) are also known or can be prepared by customary methods [J.C. Buck, F. Ellis, P. North, Tetrahedron Letters 1982, 4161–4162].

The compounds of the general formula (VII) are known per se or can be prepared by customary methods. Examples which may be mentioned are: ethyl 3-bromopropionate and ethyl chloro-methylbenzoate [compare Beilstein, Volume II, p. 256, Beilstein Volume IX, p. 458].

The compounds according to the invention show an unforeseeable useful spectrum of pharmacological action. They block the specific receptors of the leukotrienes on the target cells (for example,muscle cells) and thus act as leukotriene antagonists.

They may therefore be used in medicaments for the treatment and prophylaxis of allergic and inflammatory disorders, such as, for example, allergies, asthma, bronchitis, emphysema, shock lung, pulmonary hypertension, inflammations, oedemas, thromboses and thromboembolisms, ischaemias (peripheral, cardiac or cerebral circulatory disturbances), cardiac and renal infarcts, cardiac arrhythmias, angina pectoris, arteriosclerosis, in tissue transplants, dermatoses such as psoriasis, metastases and for cytoprotection in the gastrointestinal tract.

TEST DESCRIPTION

1. Preparation

Guinea-pigs are killed by a blow to the head and the trachea is added to a Tyrodes solution (mM NaCl 137, $MgCl_2$ 2.1, $KCl_{12.7}$, $NaH_2PO_4$0.5, $CaCl_2$2.4, $NaHCO_3$11.9, D-glucose 9.2) containing indomethacin $(3\times10^{-6}M)$. The trachea is opened longitudinally to the trachea and alternately cut transversely over ⅔ of the total organ width. The preparation is unfolded as a zig zag chain in a 10 ml organ bath containing a Tyrodes solution and an indomethancin addition $(3\times10^{-6}$ M) is added and the solution is aerated at a temperature of 37° C. with 5% $CO_2$ in oxygen. The contraction was observed with the aid of an isotonic Hugo Sachs transducer using a loading of 250–300 mg.

2. Experiment

After equilibration in the organ bath, the maximum contraction is determined with $10^{-4}$ and $3\times10^{-4}$ M histamine. The histamine is washed out and Tyrodes is exchanged for Tyrodes containing indomethacin, L-serine borate (45 mM) and L-cysteine (10 mM). After reequilibration, 10 μl of ethanol is added to one of the four preparations as a control in series. The compounds according to the invention are added in concentrations of $10^{-11}$ to $10^{-5}$ M to the other 3 preparations, in each case in increasing amounts. 15 minutes after the last addition of the compounds according to the invention or ethanol, an increasing concentration response curve for $LTD_4$ is obtained ($10^{-10}-10^{-6}$ M). After reaching the maximum $LTD_4$ concentration, the tissue preparations are discarded.

3. Results

The concentrations are standardized on the histamine-induced maximum for each preparation. The response to the compounds according to the invention, $LTD_4$ and $LTD_4$ together with the compounds according to the invention is then indicated in per cent as the response to the $LTD_4$ maximum in the corresponding control preparation. The $EC_{50}$ values (50% of the maximum $LTD_4$ contraction) of the experiments and the control experiments are determined by the root mean square deviation method. The results are used to calculate a $pk_8$ value in order to determine thereby the quantitative extent of the respective antagonism.

| Example No. | $pk_B$ |
|---|---|
| 5 | 8.1 |
| 7 | 6.1 |
| 17 | 7.3 |

The new active compounds may be converted in a manner known per se using inert non-toxic, pharmaceutically suitable excipients or solvents into the customary formulations, such as tablets, capsules, coated tablets, pills, granules, aerosols, syrups, emulsions, suspensions and solutions. In this connection, the therapeutically active compound should in each case be present in a concentration of about 0.5 to 90% by weight, preferably from 10 to 70% by weight, in the total mixture, i.e. in amounts which are sufficient in order to achieve the dosage range indicated.

The formulations are prepared, for example, by extending the active compound using solvents and/or excipients, optionally using emulsifiers and/or dispersants, where, for example, in the case of the use of water as a diluent, if appropriate organic solvents can be used as auxiliary solvents.

Examples of auxiliaries which may be mentioned are: water, non-toxic organic solvents such as paraffins (for example, mineral oil fractions), vegetable oils (for example, groundnut/sesame oil), alcohols (for example, ethyl alcohol, glycerol), glycols (for example propylene glycol, polyethylene glycol), solid excipients, such as ground natural minerals (for example kaolins, aluminas, talc, chalk), ground synthetic minerals (for example, highly disperse silica, silicates), sugars, (for example, sucrose, lactose and dextrose), emulsifiers (for example, polyoxyethylene fatty acid esters, polyoxyethylene fatty alcohol ethers, alkylsulphonates and arylsulphonates), dispersants (for example, lignin-sulphite waste liquors, methyl cellulose, starch and polyvinylpyrrolidone) and lubricants (for example magnesium stearate, talc, stearic acid and sodium lauryl sulphate).

Administration may be carried out in a customary manner, preferably orally or parenterally, in particular perlingually or intravenously. In the case of oral administration, tablets may, of course, also contain additions such as sodium titrate, calcium carbonate and dicalcium phosphate together with various additives, such as starch, preferably potato starch, gelatin and the like in addition to the excipients mentioned. Furthermore, lubricants, such as magnesium stearate, sodium lauryl sulphate and talc may additionally be used for tableting. In the case of aqueous suspensions and/or elixirs which are intended for oral administration, various flavor enhancers or colorants may be added to the active compounds in addition to the abovementioned auxiliaries.

In the case of parenteral administration, solutions of the active compound using suitable liquid excipient materials may be employed.

In general, it has proved advantageous on intravenous administration to administer amounts of about 0.01 to 10 mg/kg, preferably about 0.01 to 5 mg/kg of body weight to attain effective results. On oral administration, the dosage is generally about 0.1 to 200 mg/kg, preferably 1 to 100 mg/kg of body weight.

In spite of this, it may be necessary to deviate from the amounts mentioned, depending on the body weight or the type of administration route, on individual behavior toward the medicament, the manner of its formulation and the point in time or interval at which administration takes place. Thus, in some cases it may be sufficient to manage with less than the minimum amount previously mentioned, whereas An other cases the upper limit mentioned must be exceeded. In the case of the administration of larger amounts, it may be advisable to divide these into a number of individual doses over the day.

The indoles according to the invention may be used both in human medicine and in veterinary medicine.

PREPARATION EXAMPLES

Example 1

Methyl 6-indolecarboxylate

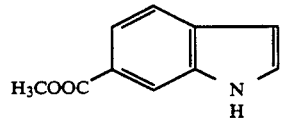

16.7 g (0.060 mol) of methyl 4-(2-dimethylaminoethenyl)-3-nitrobenzoate [prepared according to the general working procedure of L.F. Tietze and Th. Eicher, "Reaktionen und Synthesen" (Reactions and Syntheses), p. 172, Thieme, Stuttgart 1981]were hydrogenated in 300 ml of tetrahydrofuran containing 1.1 g of palladium carbon (10%). The solution was filtered for 2 hours through kieselguhr and the catalyst was washed with 50 ml of tetrahydrofuran. The solvent was removed in vacuo. In order to remove a small amount of impurity (methyl 3-amino-4-methylbenzoate), the product was washed successively with 10% strength hydrochloric acid, water and concentrated sodium chloride solution, dried over magnesium sulphate and concentrated on a rotary evaporator. Yield: 9.9 g (94% of

Example 2

Methyl 3-formyl-6-indolecarboxylate

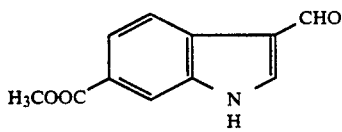

4.3 ml of phosphorus oxychloride was added dropwise with stirring and cooling (0° C) to 14 ml of dimethylformamide and the mixture was stirred for a further 15 minutes at 0° C. After this, a solution of 8.6 g (0.049 mol) of the compound from Example 1 in 13 ml of dimethylformamide was added dropwise at room temperature, whereupon the temperature did not rise above 30° C. The solution was stirred for a further 3 hours at 35° C., added dropwise to ice water and adjusted to pH 7 using 2 N sodiumhydroxide solution. The solution was washed with methylene chloride and again adjusted to pHi using 2 N hydrochloric acid. A precipitate deposited overnight, which was filtered off with suction and dried. Yields 6.4 g (64% of theory) of white powder $R_f$ ( 9: 1, CHaC 12 ( MeOH ) =0.54 $R_f$ (95:5, CH$_2$Cl$_2$/MeOH)=0.38

Example 3

Methyl 1-(2-ethoxycarbonyl)ethyl-3-formyl-6-indolecarboxylate

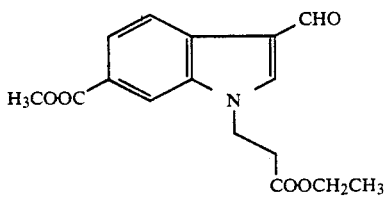

3.9 g (0.019 mol) of indole aldehyde, of the compound from Example 2, 4.0 g (0.022 mol) of ethyl 3-bromopropionate, 5.3 g (0.038 mol) of potassium carbonate and 30 ml of dimethylformamide was stirred at 100° C. for 3 hours. The solvent was removed in vacuo and the residue was stirred with 50 ml of water and cooled to 5° C. The white amorphous precipitate was filtered off with suction, washed with water and dried in vacuo over phosphorus pentoxide. Yield: 5.3 g (90% of theory) Melting point: 129° C. $R_f$(9:1, CH$_2$Cl$_2$MeOH)=0.85

Example 4

Methyl 3-{2-[4-(4-phenoxybutoxy)phenyl]-2-(Z)-ethenyl}6-indolecarboxylate (4a) and E-isomer (4b)

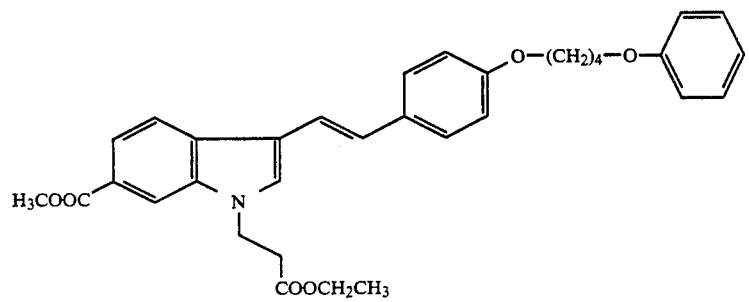

70 ml (0.026 mol) of freshly prepared lithium diisopropylamine are added dropwise under nitrogen at −78° C. in tetrahydrofuran (0.37 mol) to a solution of 15.3 g (0.026 mol) of 4-(4-phenoxybutoxy)benzyltriphenylphosphonium bromide in 25 ml of absolute tetrahydrofuran. The reaction solution was stirred at −20° C. for 30 minutes and cooled to −78° C. A solution of 7.1 g (0.023 mol) of indole aldehyde of the compound from Example 3 in 100 ml of absolute tetrahydrofuran was then added dropwise in the course of 30 minutes. The mixture was stirred at room temperature for 2.5 hours and diluted with water, and the solution was extracted a number of times using ether. The organic phase was washed with saturated sodium hydrogen carbonate solution, dried using magnesium sulphate and evaporated. The residue was chromatographed on 300 g of silica gel using petroleum ether/ether 1:1. In this way, a mixture of the cis- and trans-isomers was obtained which was chromatographed again on 800 g of silica gel using 1/1 petroleum ether/ether. In this manner, three fractions were obtained, of which the first contained pure cis- and the third pure trans-isomer. After chromatography of the mixed fractions (2.0 g) on 400 g of silica gel, two pure isomers were obtained. Yield: 5.43 g (43% of theory) of cis-isomer (4a) 3.99 g (32% of theory) of trans-isomer (4b) (Petroleum ether/ether 1/1) cis-isomer=0.30; trans-isomer =0.20, $^1$H-NMR (DMSO): δ=6.55 (—CH=CH-cis, AB system, I=12.5 Hz);

7.20 (-CH=CH-trans, AB system, I=16.0 Hz).

Example 5

1-(2-Ethoxycarbonyl )-ethyl-3-( {2-[4-( 4-phenoxybutoxy)phenyl ]-2-(Z )-ethenyl }-6-indole carboxylic acid

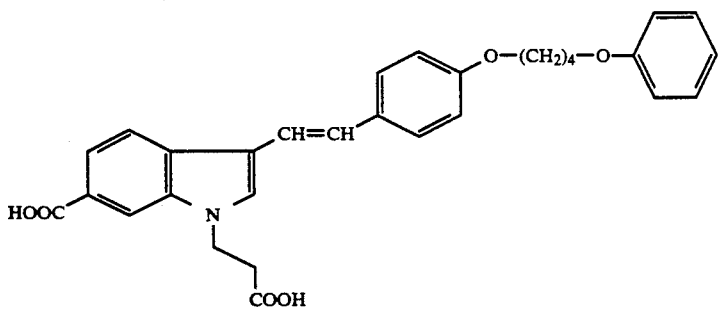

7.9 g (0.015 mol) of methyl indolecarboxylate of the compound from Example 4a were dissolved in 90 ml of tetrahydrofuran, 15 ml of methanol were added and the mixture was cooled to 0° C. 20 ml of 2 N sodium hydroxide solution were added dropwise and the mixture was allowed to come to room temperature overnight. It was diluted with water and acidified to pH 6 using 2 N sulphuric acid. The turbid solution was extracted a number of times using ethyl acetate, then washed with water and dried over magnesium sulphate. 6.80 g (94% of theory) of pale yellow crystals were obtained from the evaporated solution in ethyl acetate. Melting point: 185° C. $R_f$ (RP-HPLC); 7.990 UV ( $CH_3CN$ ): λ max: 208, 248, 293 and 323 nm.

Example 6 to 16, which are shown in the following table, were prepared analogously to the proced. ure for Example 5.

TABLE 1

| Ex. No. | A | B | G | Double bond isomer | $R_f$ or m.p. (°C.) |
|---|---|---|---|---|---|
| 6 | —(CH₂)₂—COOH | (2-substituted phenyl with O—(CH₂)₄—O—phenyl) | 6-COOH | trans | 0.42 (A) |
| 7 | —(CH₂)₂—COOH | (3-substituted phenyl with O—(CH₂)₄—O—phenyl) | 6-COOH | cis | 0.45 (A) |
| 8 | —(CH₂)₂—COOH | (3-substituted phenyl with O—(CH₂)₄—O—phenyl) | 6-COOH | trans | 0.30 (A) |
| 9 | —(CH₂)₂—COOH | (4-substituted phenyl with O—(CH₂)₄—O—phenyl) | 6-COOH | trans | 210° C. |
| 10 | —(CH₂)₂—CONHSO₂Ph | (4-substituted phenyl with O—(CH₂)₄—O—phenyl) | 6-CONH—SO₂—phenyl | trans | 0.61 (A) |

TABLE 1-continued
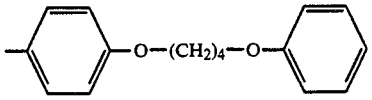
| Ex. No. | A | B | G | Double bond isomer | |
|---|---|---|---|---|---|
| 11 | —CH$_3$ | 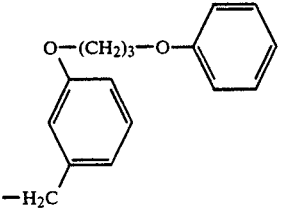 | 6-COOH | trans | 0.26 (C) |
| 12 | —(CH$_2$)$_2$—COOH | 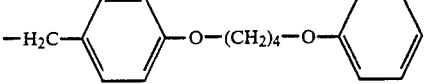 | H | cis | 0.34 (B) |
| 13 | —(CH$_2$)$_2$—COOH | 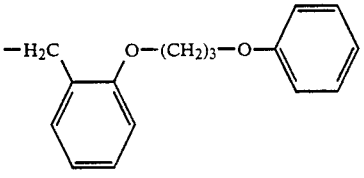 | 6-COOH | trans | 173° C. |
| 14 | —(CH$_2$)$_2$—COOH | 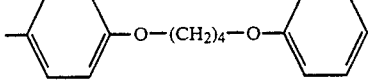 | 6-COOH | cis | 109° C. |
| 15 | —(CH$_2$)$_2$—COOH | 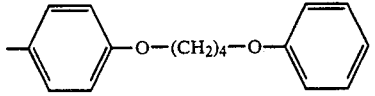 | 4-COOH | cis | 143° C. |
| | | | | | R$_f$, m.p. (°C.) or retention time (min) |
|---|---|---|---|---|---|
| 16 | —(CH$_2$)$_2$—COOH | 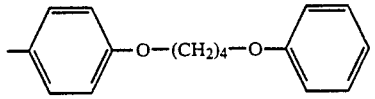 | 4-COOH | trans | 149–150° C. |
| 17 | —CH$_2$—COOH | 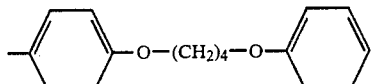 | 6-COOH | trans | 167° C. |
| 18 | —(CH$_2$)$_2$—COONa | 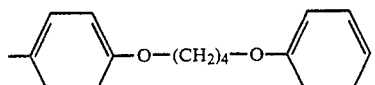 | 5-CN | trans | 8.44 (D) |
| 19 | —(CH$_2$)$_2$—COONa | | 5-CN | cis | 8.43 (D) |

TABLE 1-continued

| Ex. No. | A | B | G | | Double bond isomer | |
|---|---|---|---|---|---|---|
| 20 | —(CH₂)₂—COONa | —CH₂—⌬—O—(CH₂)₄—O—⌬ | 5-CN | | trans | 8.56 (D) |
| 21 | —(CH₂)₂—COONa | —CH₂—⌬—O—(CH₂)₄—O—⌬ | 5-CN | | cis | 8.63 (D) |
| 22 | —(CH₂)₂—COONa | —CH₂—⌬—O—(CH₂)₄—O—⌬ | 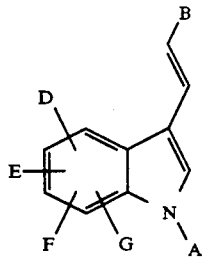 | | cis | 0.52 (A) |
| 23 | —(CH₂)₂—COOH | —⌬—O—(CH₂)₄—O—⌬ | 5-COOH | | trans | 0.38 (A) |

The following eluents were used:
(A) = Dichloromethane/methanol 9:1
(B) = Ethyl acetate/butanol/acetic acid 9:1:0.1
(C) = Toluene/ethyl acetate 8:2
(D) = Nucleosil ® 120-5 C 18, 5 μm, 125 × 4 mm 10–90% acetonitrile containing 10 mM H₃PO₄, + 10% acetonitrile, flow: 2 ml/min, room temperature It will be appreciated that the instant specification is set forth by way of illustration and not limitation, and that various modifications and changes may be made without departing from the spirit and scope of the present invention.

What is claimed is:

1. A method for antagonizing leukotriene in a patient in need thereof which comprises administering to such patient an amount effective therefor of an indole derivative of the formula:

(I)

in which

A represents straight-chain or branched alkyl having up to 10 carbon atoms, which is unsubstituted or substituted by cyclopropyl, cyclopentyl, cyclohexyl, fluorine, chlorine, bromine, hydroxyl, carboxyl, cyano, straight-chain or branched alkoxy or alkoxycarbonyl, each having up to 8 carbon atoms; represents straight-chain or branched alkyl or alkenyl each having 12 to 16 carbon atoms, each of which is unsubstituted or substituted by fluorine, chlorine, bromine, carboxyl, hydroxyl, straight-chain or branched alkoxy, acyl or alkoxycarbonyl each having up to 8 chain atoms, or by phenyl which may in turn be monosubstituted to trisubstituted by identical or different substituents selected from the group consisting of fluorine, chlorine, bromine, carboxyl, cyano and hydroxyl, or by a group of the formula —Y—(CH₂)ₙ—X—R³;

in which

X and Y are identical or different and represent oxygen, sulfur or a direct bond;

n represents a number 1,2,3,4,5 or 6; and

R³ represents phenyl or naphthyl, each of which is unsubstituted or substituted by hydroxyl, carboxyl, cyano, fluorine, chlorine, bromine or by straight-chain or branched alkoxy, acyl or alkoxycarbonyl, each having up to 8 carbon atoms; or B represents phenyl, which is unsubstituted or monosubstituted or disubstituted by identical or different substituents selected from the group consisting of fluorine, chlorine, bromine, nitro and hydroxyl, or by a group of the formula —Y—(CH₂)ₙ—X—R³;

D,E,F and G are identical or different and represent hydrogen, fluorine, chlorine, bromine, cyano, carboxyl, straight-chain or branched alkyl, acyl or akoxycarbonyl each having up to 8 carbon atoms, thienyl, furyl, pyrryl or tetrazolyl; or represent a group of the formula —CO—NH—SO₂—R¹, in which R¹ represents phenyl or naphthyl, each of which is unsubstituted or monosubstituted or disubstituted by identical or different substituents selected from the group consisting of carboxyl, fluorine, chlorine, bromine, cyano, nitro or by straight-chain or branched alky, alkoxy or alkoxycarbonyl, each having up to 8 carbon atoms, or by phenyl or naphthyl, which are in turn monosubstituted to trisubstituted by identical or different substituents selected from the group consisting of carboxyl, straight-chain or branched alkyl, alkylthio, alkoxy or akloxycarbonyl, each having up to 8 carbon atoms, or by a group of the formula —NH—$R^2$;

in which
$R^2$ represents hydrogen, straight-chain or branched alkyl or acyl each having up to 6 carbon atoms; or a salt thereof.

2. The method according to claim 1, wherein the administration of the indole derivative is for the treatment and/or propylaxis of allergic and/or inflammatory disorders.

* * * * *